(12) United States Patent
Erland

(10) Patent No.: US 9,078,759 B2
(45) Date of Patent: Jul. 14, 2015

(54) STOMA-LEAKAGE COLLECTING DEVICE, ATTACHMENT PLATE AND ASSEMBLY THEREOF

(75) Inventor: Jofrid Erland, Stavanger (NO)

(73) Assignee: Erland AS, Stavanger (NO)

( * ) Notice: Subject to any disclaimer, the term of this patent is extended or adjusted under 35 U.S.C. 154(b) by 101 days.

(21) Appl. No.: 13/880,687

(22) PCT Filed: Nov. 24, 2011

(86) PCT No.: PCT/NO2011/000332
§ 371 (c)(1),
(2), (4) Date: Apr. 19, 2013

(87) PCT Pub. No.: WO2012/070953
PCT Pub. Date: May 31, 2012

(65) Prior Publication Data
US 2013/0237943 A1 Sep. 12, 2013

(30) Foreign Application Priority Data
Nov. 25, 2010 (NO) .................................. 20101658

(51) Int. Cl.
*A61F 5/448* (2006.01)
*A61F 5/44* (2006.01)
(Continued)

(52) U.S. Cl.
CPC ............... *A61F 5/4401* (2013.01); *A61F 5/445* (2013.01); *A61F 5/448* (2013.01); *A61F 5/449* (2013.01)

(58) Field of Classification Search
CPC ....... A61F 5/4401; A61F 5/445; A61F 5/448; A61F 5/449

USPC ................................................... 604/336–338
See application file for complete search history.

(56) References Cited

U.S. PATENT DOCUMENTS 3,906,951 A 9/1975 Chen
4,085,752 A 4/1978 Canale
(Continued)

FOREIGN PATENT DOCUMENTS

GB 2465742 A 6/2010
WO 2010034966 A2 4/2010

OTHER PUBLICATIONS

Norwegian Search Report for priority application No. 20101658, dated Apr. 15, 2011.
(Continued)

*Primary Examiner* — Susan Su
(74) *Attorney, Agent, or Firm* — Andrus Intellectual Property Law, LLP

(57) ABSTRACT

Stoma-leakage collecting device, attachment plate and assembly thereof, wherein the collecting device is structured for use together with an ordinary attachment plate for a stoma waste pouch. The collecting device is comprised of a plate-shaped body having a surface which is larger than the surface of the attachment plate. The collecting device comprises an inner, liquid-absorbent material; an outer, liquid-tight material; and an opening through the outer and inner material, respectively. At least the opening in the outer material is structured for placement around a stoma communication opening in the attachment plate, wherein at least the opening in the outer material is smaller than the smallest transverse dimension of the attachment plate. At least a radially inner rim area located around the opening in the outer material is structured in a manner allowing it to be attached in a liquid-tight manner to a rim area of the attachment plate.

21 Claims, 8 Drawing Sheets

(51) Int. Cl.
*A61F 5/445* (2006.01)
*A61F 5/449* (2006.01)

(56) References Cited

U.S. PATENT DOCUMENTS

| | | | |
|---|---|---|---|
| 4,701,169 A * | 10/1987 | Steer | 604/344 |
| 4,865,594 A | 9/1989 | Thomas | |
| 5,013,307 A | 5/1991 | Broida | |
| 5,185,008 A * | 2/1993 | Lavender | 604/338 |
| 5,626,570 A | 5/1997 | Gallo | |
| 5,785,695 A * | 7/1998 | Sato et al. | 604/339 |
| 6,709,421 B1 * | 3/2004 | Falconer | 604/335 |
| 6,840,924 B2 * | 1/2005 | Buglino et al. | 604/337 |
| 2003/0004477 A1 * | 1/2003 | Nielsen et al. | 604/336 |
| 2003/0073965 A1 * | 4/2003 | Leise et al. | 604/336 |
| 2005/0177119 A1 * | 8/2005 | Tsai | 604/332 |
| 2007/0203466 A1 * | 8/2007 | Pedersen et al. | 604/333 |
| 2007/0219514 A1 * | 9/2007 | Strobech | 604/336 |
| 2008/0071236 A1 * | 3/2008 | Lee | 604/333 |
| 2009/0216208 A1 * | 8/2009 | Leisner | 604/344 |
| 2010/0204664 A1 * | 8/2010 | Bach et al. | 604/344 |
| 2010/0217215 A1 * | 8/2010 | Lykke et al. | 604/344 |
| 2012/0283678 A1 * | 11/2012 | Nguyen-DeMary et al. | 604/337 |
| 2012/0302981 A1 * | 11/2012 | Lam | 604/344 |
| 2013/0035654 A1 * | 2/2013 | Friske | 604/344 |
| 2013/0226117 A1 * | 8/2013 | Hansen et al. | 604/338 |
| 2014/0249494 A1 * | 9/2014 | Bird et al. | 604/344 |

OTHER PUBLICATIONS

International Search Report for parent application PCT/NO2011/000332, having a mailing date of Mar. 8, 2012.
Written Opinion for parent application PCT/NO2011/000332, having a mailing date of Mar. 8, 2012.
Preliminary Report for parent application PCT/NO2011/000332, having a mailing date of Nov. 12, 2012.

* cited by examiner

STOMA-LEAKAGE COLLECTING DEVICE, ATTACHMENT PLATE AND ASSEMBLY THEREOF

CROSS-REFERENCE TO RELATED APPLICATIONS

This application is the U.S. national stage application of International Application No. PCT/NO2011/000332, filed Nov. 24, 2011, which International application was published, on May 31, 2012 as International Publication No. WO 2012/070953 A1 in the English language and which application is incorporated herein by reference. The International application claims priority of Norwegian Patent Application No. 20101658, filed. Nov. 25, 2010, which application is incorporated herein by reference.

FIELD OF THE INVENTION

The present invention concerns a stoma-leakage collecting device, an attachment plate and an assembly of said collecting device and attachment plate. The invention is directed toward stoma-operated or reservoir-operated patients.

BACKGROUND OF THE INVENTION

A consequence of such operations is that the patients have an artificial opening in the body. Such an opening is generally used for discharge of various more or less liquid-containing waste products, such as feces and urine. Typically, this relates to patients having an extracted intestine through which feces is conducted out of the body and further into a suitable waste pouch. Generally, such a waste pouch will be attached to the body of the patient via a fitted attachment plate. Some waste pouches are fixed to the attachment plate, for example by means of an adhesive agent or fusion welding, whereas other waste pouches may be releasably attached to the attachment plate. Further, such an attachment plate is either provided with, or may be provided with, an adhesive agent for releasable attachment to the body around the discharge opening (the stoma). In this manner, the waste pouch and the attachment plate may be readily replaced when required.

For most patients, both the attachment and the replacement of the attachment plate and the waste pouch are reasonable straightforward tasks, but for some patients such a stoma may involve partly very large and unpleasant problems. This generally relates to patients having large and/or complicated stomas, for example with abscesses, and possibly with surgery-related cicatrizations (scarring) and/or with skin folds causing unsatisfactory attachment/adhesion of the attachment plate to the body and/or around the stoma. For patients having such problems, unintentional stoma leakages may therefore readily arise between the attachment plate and the body. Such a leakage may easily soil clothes, garments and/or objects in vicinity of the patient. Normally, this will be perceived as very unpleasant to the patient and anybody else in vicinity of the patient. Advantageously, and for this reason, the patient could be provided with a stoma-leakage collecting device as an additional guarantee against such unpleasantnesses. Such a collecting device will be an addition to, and not a replacement for, ordinary stoma waste pouches and related equipment.

PRIOR ART AND DISADVANTAGES THEREOF

U.S. Pat. No. 5,013,307 appears to represent the closest prior art. This patent publication concerns an absorbent pad for use in context of a flexible attachment plate for a stoma waste pouch; this in similarity to the initial discussion on such equipment. The absorbent pad comprises a liquid-transporting and liquid-absorbent inner core with a liquid-tight outer layer. The pad is provided with a peripheral adhesive rim, and also a central opening structured in a manner allowing it to be attached around a corresponding pipe socket onto which the stoma waste pouch is attached for communication with a stoma on a patient. In order to fit in a tight-fitting manner around the pipe socket, an inner rim area around the opening in the pad may be crimped or formed with radial slits, possibly be provided with perforated, concentric rings that may be removed as needed for fitting onto the pipe socket. In order to allow for easier attachment around, or removal from, the pipe socket of the attachment plate, the pad may also be provided with a cut edge extending from the central opening of the pad and outward to the peripheral adhesive rim thereof. By so doing, the pad may be treaded around the pipe socket of the attachment plate, and in such a way that the cut edges overlap each other and possibly are connected by means of an adhesive agent, an adhesive strip or tape.

Even though U.S. Pat. No. 5,013,307 describes a technical solution addressing the same problem as the present invention, there is one important problem that U.S. Pat. No 5,013,307 does not mention or solves in a satisfactory manner. The publication does not address the problem of potential stoma leakage via an area between the attachment plate and the central opening of the pad. It is indeed mentioned that the inner rim area around the central opening is to fit in a tight-fitting manner around the pipe socket, however this is not a leakage-free connection preventing stoma leakage via this area. If such a stoma leakage arises quickly and is of a relatively large extent, for example mixed with overpressured gas, an undesirable leakage may quickly arise via this area. Such a leakage problem may be enhanced further if this inner rim area is formed with radial slits or perforated, concentric rings for fitting to the pipe socket, or if the pad is provided with said cut edge extending from the central opening of the pad and outward to the peripheral adhesive rim thereof. As such, the publication neither mentions nor indicates a concrete solution to this leakage problem which, on the other hand, the present invention does.

Moreover, U.S. Pat. No. 4,085,752 is mentioned as background prior art, also concerning an absorbent pad for use together with a stoma waste pouch, as well as U.S. Pat. No. 5,626,570, which concerns a belt for use together with a flexible attachment plate for a stoma waste pouch.

OBJECTS OF THE INVENTION

The object of the invention is to remedy or reduce at least one disadvantage of the prior art in the field.

A more specific object of the invention is to provide at least one technical solution which at least reduces partly very large and unpleasant problems associated with unintentional stoma leakages from attachment plates for stoma waste pouches.

HOW THE OBJECTS ARE ACHIEVED

The objects are achieved by virtue of features disclosed, in the following description and in the subsequent claims.

According to a first aspect of the invention, a stoma-leakage collecting device structured for use together with an ordinary, per se attachment plate for a stoma waste pouch is provided, the attachment plate being structured in a manner allowing it to be releasably attached to a body and around a stoma on the body;

wherein the collecting device is comprised of a plate-shaped body having a surface which is larger than the surface of the attachment plate, and wherein the collecting device comprises;

an inner, liquid-absorbent material for collection of leakage material from said stoma;

an outer, liquid-tight material covering the inner material for inclusion of said leakage material; and an opening through the outer material and the inner material, respectively, wherein at least the opening in the outer material is structured in a manner allowing it to be placed around a corresponding stoma communication opening in the attachment plate, and wherein at feast the opening in the outer material is smaller than the smallest transverse dimension of the attachment plate.

The distinctive characteristic of the stoma-leakage collecting device is that at least a radially inner rim area located around the opening in the outer material, is structured in a manner allowing it to be attached in a liquid-tight manner to a rim area of the attachment plate. By so doing, leakage between the collecting device and the attachment plate is prevented.

This attachment plate is of an ordinary type. For such attachment plates, the stoma waste pouch may be fixed to the outside of the attachment plate, or the waste pouch may be releasably attached to the attachment plate.

Typically, said leakage material from a stoma will be comprised of various more or less liquid-containing waste products, such as feces and urine. Further, such liquid-containing waste products wilt typically leak out between the attachment plate and the body of a patient, i.e. via the inside of the attachment plate.

The outer, liquid-tight material of the collecting device may, for example, be comprised of a suitable plastics material, whereas the inner, liquid-absorbent material of the collecting device may comprise one or more layers of liquid-absorbent and possibly liquid permeable fabrics. Typically, such fabrics are found in nappies and sanitary napkins, including so-called super-absorbent fabrics based on, for example, polyester or similar fabrics, such as described in U.S. Pat. No. 5,013,307, among other places. Such materials are to be considered as prior art and, hence, will not be described in further detail herein.

In an advantageous embodiment, at least the radially inner rim area of the collecting device may be provided with an adhesive agent for liquid-tight attachment to the attachment plate. This is a simple way of providing a liquid-tight connection between the collecting device and the attachment plate.

Other liquid-tight connections may possibly also be used for such a liquid-tight connection between the collecting device and the attachment plate. Thus, the radially inner rim area of the collecting device may comprise a continuous leakage barrier, for example of a rubberized material, and also a hook and loop fastener element (Velcro element). Thereby, this hook and loop fastener element may be connected together with a cooperating hook and loop fastener element disposed on the attachment plate, and such that said leakage barrier is forced in a liquid-sealing manner against the attachment plate during the interconnection. This, however, is a relatively complicated manner of providing a liquid-tight connection between the collecting device and the attachment plate.

The opening in the inner, liquid-absorbent material of the collecting device may also be smaller than the smallest transverse dimension of the attachment plate, wherein also a radially inner rim area located around the opening in the inner material, is provided with an adhesive agent for liquid-tight attachment to the attachment plate. By so doing, both the outer, liquid-tight material and the inner, liquid-absorbent material may be attached to the attachment plate by means of a suitable adhesive agent.

As an alternative, the opening in the inner, liquid-absorbent material of the collecting device may be larger than the attachment plate. Thereby, the attachment plate may be included in this larger opening in the inner material, whereas only the radially inner rim area of the outer, liquid-tight material is attached to the attachment plate by means of a suitable adhesive agent. In this context, the opening in the inner material advantageously may have a shape that fits around the periphery of the attachment plate.

Further, this inner material may be releasably arranged relative to the outer material. By so doing, the inner, liquid-absorbent material may be replaced when required, however without having to replace the outer, liquid-tight material at the same time. This may prove useful in context of smaller leakages or in situations where little time is available for replacement of the entire collecting device and possibly the attachment plate.

Yet further, an outside of the radially inner rim area of the collecting device may be provided with an adhesive agent for liquid-tight attachment to an inside of the attachment plate. By so doing, the collecting device is structured for placement between the attachment plate and the body of the patient.

As an alternative, an inside of the radially inner rim area of the collecting device may be provided with an adhesive agent for liquid-tight attachment to an outside of the attachment plate. By so doing, the collecting device is structured for placement between the attachment plate and said stoma waste pouch.

Further, said adhesive agent may be covered by a releasable cover material, for example a cover strip or a cover paper. This cover material is torn off immediately before the radially inner rim area of the collecting device is to be fixedly adhered to the attachment plate. By so doing, attachment of the adhesive agent to unwanted places during the connecting operation is avoided.

Although not necessarily having to attach a radially outer rim area of the collecting device in a liquid-tight manner to the body of a patient, for example in context of smaller stoma leakages, it may prove advantageous for the outer rim area to be provided with an adhesive agent for releasable and liquid-tight attachment to the body in an area located outside the attachment plate. By so doing, the collecting device is structured for complete liquid-tight inclusion of leakage material from said stoma. This may prove particularly useful if the collecting device is to be used for a relatively long time and/or if the particular patient is suffering from relatively fast and large stoma leakages, for example leakages mixed with over-pressured gas. Also in this case, the adhesive agent on the radially outer rim area of the collecting device may be covered by a releasable cover material, for example a cover strip or a cover paper.

Yet further, such a radially outer rim area of the collecting device may be provided with a continuous leakage barrier, for example a leakage barrier comprising a rubberized material. Such a leakage barrier may possibly be used as an addition or alternative to an outer rim area provided with an adhesive agent.

Moreover, such a radially outer rim area of the collecting device may be structured so as to be elastically flexible for forcing the radially outer rim area against the body. This may prove very useful if this outer rim area also is provided with a continuous leakage barrier; cf. the preceding embodiment.

Further, the collecting device may be structured in a manner allowing it to be attached to the body in one of the following ways:
- the collecting device is connected to a belt for attachment around the body;
- the collecting device is incorporated in an elastic pad for attachment around the body; and
- the collecting device is incorporated in a nappy, for example a pant nappy, for attachment around the body.

All of these three embodiments constitute practical solutions for allowing the present stoma-leakage collecting device to be worn together with an attachment plate and a stoma waste pouch on the body of a patient.

According to a second aspect of the invention, an attachment plate for a stoma waste pouch is provided, the plate of which is complementary to said stoma-leakage collecting device, the attachment plate being structured in a manner allowing it to be releasably attached to a body and around a stoma on the body;
- wherein the attachment plate is structured for use together with a stoma-leakage collecting device comprised of a plate-shaped body, wherein the attachment plate has a surface which is smaller than the surface of the collecting device; and
- wherein the collecting device comprises:
  - an inner, liquid-absorbent material for collection of leakage material from said stoma;
  - an outer, liquid-tight material covering the inner material for inclusion of said leakage material; and
  - an opening through the outer material and the inner material, respectively, wherein at least the opening in the outer material is structured in a manner allowing it to be placed around a corresponding stoma communication opening in the attachment plate, and wherein at least the opening in the outer material is smaller than the smallest transverse dimension of the attachment plate.

The distinctive characteristic of the attachment plate is that a rim area, for example a radially outer rim area, of the attachment plate is structured in a manner allowing it to be attached in a liquid-tight manner to a radially inner rim area of the collecting device, the rim area of which is located at least around the opening in the outer material of the collecting device. By so doing, leakage between the attachment plate and the collecting device is prevented.

Typically, said leakage material from a stoma will be comprised of various more or less liquid-containing waste products, such as feces and urine. Further, such liquid-containing waste products will typically leak out between the attachment plate and the body of a patient, i.e. via the inside of the attachment plate.

Advantageously, the attachment plate may be comprised of a relatively thin and flexible plastics material of a suitable type. Thereby, the attachment plate will be pliable and easy to mount onto the body of the patient and will also be comfortable to wear for the patient.

In an advantageous embodiment, the rim area of the attachment plate may be provided with a suitable adhesive agent for liquid-tight attachment to the radially inner rim area of the collecting device. This is a simple way of providing a liquid-tight connection between the attachment plate and the collecting device.

Other liquid-tight connections may possibly also be used for such liquid-tight connection between the attachment plate and the collecting device. Thus, the rim area of the attachment plate may comprise a continuous leakage barrier, for example of a rubberized material, and also a hook and loop fastener element (Velcro element).

Thereby, this hook and loop fastener element may be connected together with a cooperating hook and loop fastener element disposed on the radially inner rim area of the collecting device, and such that said leakage barrier is forced in a liquid-sealing manner against the inner rim area of the collecting device during the interconnection. This, however, is a relatively complicated manner of providing a liquid-tight connection between the attachment plate and the collecting device.

According to one embodiment, an inside of the rim area of the attachment plate may be provided with an adhesive agent for liquid-tight attachment to an outside of the collecting device. By so doing, the rim area of the attachment plate may be adhered to a dedicated area on the outside of the collecting device.

According to another embodiment, an outside of the rim area of the attachment plate may be provided with an adhesive agent for liquid-tight attachment to an inside of the collecting device. By so doing, the rim area of the attachment plate may be adhered to a dedicated area on the inside of the collecting device.

Furthermore, said adhesive agent may be covered by a releasable cover material, for example a cover strip or a cover paper, to avoid that the adhesive agent attaches to unwanted places during the connecting operation.

According to a third aspect of the invention, an assembly of said stoma-leakage collecting device and an attachment plate for a stoma waste pouch is provided, the attachment plate being structured in a manner allowing it to be releasably attached to a body and around a stoma on the body;
- wherein the collecting device is comprised of a plate-shaped body having a surface which is larger than the surface of the attachment plate, and wherein the collecting device comprises;
  - an inner, liquid-absorbent material for collection of leakage material from said stoma;
  - an outer, liquid-tight material covering the inner material for inclusion of said leakage material; and
  - an opening through the outer material and the inner material, respectively, wherein at least the opening in the outer material is placed around a corresponding stoma communication opening in the attachment plate, and wherein at least the opening in the outer material is smaller than the smallest transverse dimension of the attachment plate.

The distinctive characteristic of the assembly is that a radially inner rim area of the collecting device located at least around the opening in the outer material of the collecting device, is connected in a liquid-tight manner to a rim area, for example a radially outer rim area, of the attachment plate. By so doing, leakage between the collecting device and the attachment plate is prevented.

This attachment plate may either be of an ordinary type, or it may be an attachment plate according to the second aspect of the invention.

Typically, said leakage material from a stoma will be comprised of various more or less liquid-containing waste products, such as feces and urine. Further, such liquid-containing waste products will typically leak out between the attachment plate and the body of a patient, i.e. via the inside of the attachment plate.

Otherwise, the preceding comments concerning the collecting device and the attachment plate also apply to the present assembly thereof.

The present assembly of said stoma-leakage collecting device and attachment plate, which possibly also has a stoma waste pouch attached thereto, may prove advantageous especially to patients having a need for a simple and fast combination solution for ensuring that stoma waste is collected in a suitable bag, and also for ensuring that possible unintentional leakages between such an attachment plate and the body of a patient are collected. In this context, it may relate to patients having, for example, reduced vigour and/or dexterity.

According to a first embodiment of the assembly, the radially inner rim area of the collecting device may be fixedly adhered to the rim area of the attachment plate. In this context, an outside of the radially inner rim area of the collecting device may be fixedly adhered to an inside of the rim area of the attachment plate. By so doing, the collecting device is attached to the inside of the attachment plate. As an alternative to this, an inside of the radially inner rim area of the collecting device may be fixedly adhered to an outside of the rim area of the attachment plate. By so doing, the collecting device is attached to the outside of the attachment plate. These are ways of quickly providing a liquid-tight connection between the collecting device and the attachment plate.

According to a second embodiment of the assembly, the radially inner rim area of the collecting device and the rim area of the attachment plate may be integrated together. In this context, the radially inner rim area of the collecting device and the rim area of the attachment plate may be comprised of fusible material, wherein the radially inner rim area of the collecting device and the rim area of the attachment plate are integrated together via fusion welding. As an alternative to this, the radially inner rim area of the collecting device and the rim area of the attachment plate may be comprised of formable material, wherein the radially inner rim area of the collecting device and the rim area of the attachment plate are integrated together via a mould casting process.

Further, the opening in the inner material of the collecting device may also be smaller than the smallest transverse dimension of the attachment plate, wherein also a radially inner rim area of the collecting device located around the opening in the inner material of the collecting device, is connected in a liquid-tight manner to the rim area of the attachment plate. By so doing, both the outer, liquid-tight material and the inner, liquid-absorbent material may be connected in a liquid-tight manner to the radially outer rim area of the attachment plate.

As an alternative, the opening in the inner material of the collecting device may be larger than the attachment plate. Thereby, the attachment plate is included in the opening in the inner material, whereas only the radially inner rim area of the outer material is connected in a liquid-fight manner to the rim area of the attachment plate. In this context, the opening in the inner material of the collecting device advantageously may have a shape that fits around the periphery of the attachment plate.

Further, the inner material of the collecting device may be releasably arranged relative to the outer material of the collecting device. By so doing, the inner, liquid-absorbent material may be replaced when required, however without having to replace the outer, liquid-tight material at the same time. This may prove useful in context of smaller leakages or in situations where little time is available for replacement of the entire assembly.

Although not necessarily having to attach a radially outer rim area of the collecting device of the assembly in a liquid-tight manner to the body of a patient, for example in context of smaller stoma leakages, a radially outer rim area of the collecting device advantageously may be provided with an adhesive agent for releasable and liquid-tight attachment to the body in an area located outside the attachment plate. By so doing, the assembly is structured for complete liquid-tight inclusion of leakage material from said stoma. This may prove particularly useful if the assembly is to be used for a relatively long time and/or if the particular patient is suffering from relatively fast and large stoma leakages, for example leakages mixed with over-pressured gas. Also in this case, the adhesive agent on the radially outer rim area of the collecting device may be covered by a releasable cover material, for example a cover strip or a cover paper.

Yet further, such a radially outer rim area of the collecting device of the assembly may be provided with a continuous leakage barrier, for example a leakage barrier comprising a rubberized material. Such a leakage barrier may possibly be used as an addition or alternative to an outer rim area provided with an adhesive agent.

Moreover, such a radially outer rim area of the collecting device of the assembly may be structured so as to be elastically flexible for forcing the radially outer rim area against a body. This may prove very useful if this outer rim area also is provided with a continuous leakage barrier; cf. the preceding embodiment.

Further, the assembly may be structured in a manner allowing if to be attached to the body in one of the following ways;
 the collecting device is connected to a belt for attachment around the body;
 the collecting device is incorporated in an elastic pad for attachment around the body; and
 the collecting device is incorporated in a nappy, for example, in a pant nappy, for attachment around the body.

All of these three embodiments constitute practical solutions for allowing the present assembly to be worn together with a potential stoma waste pouch on the body of a patient.

Hereinafter, some non-limiting examples of embodiments of the invention are described.

SHORT DESCRIPTION OF THE FIGURES OF THE EXEMPLARY EMBODIMENTS

Figure 8:
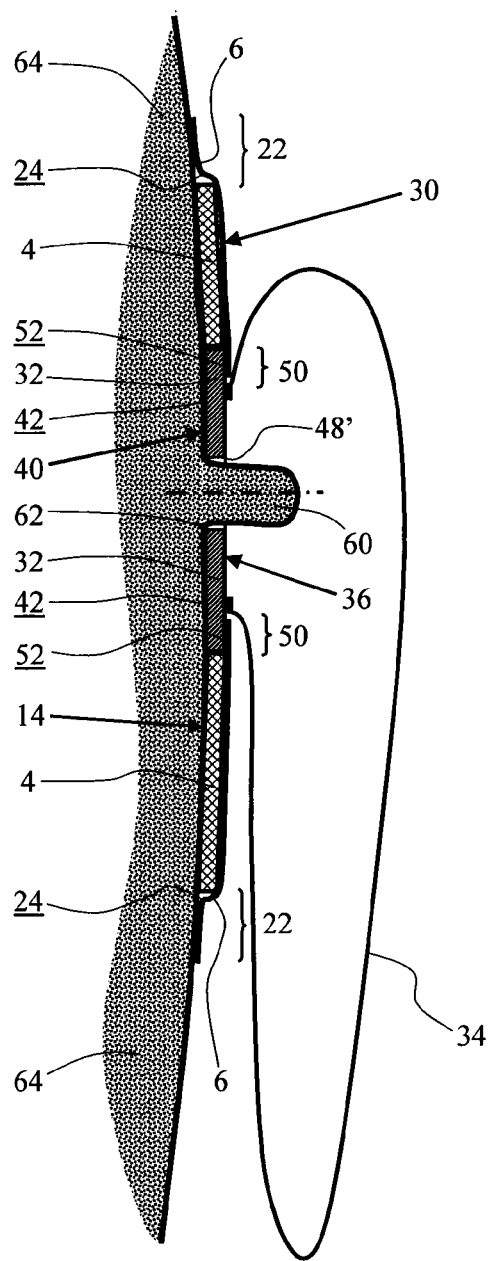
Figure 9:
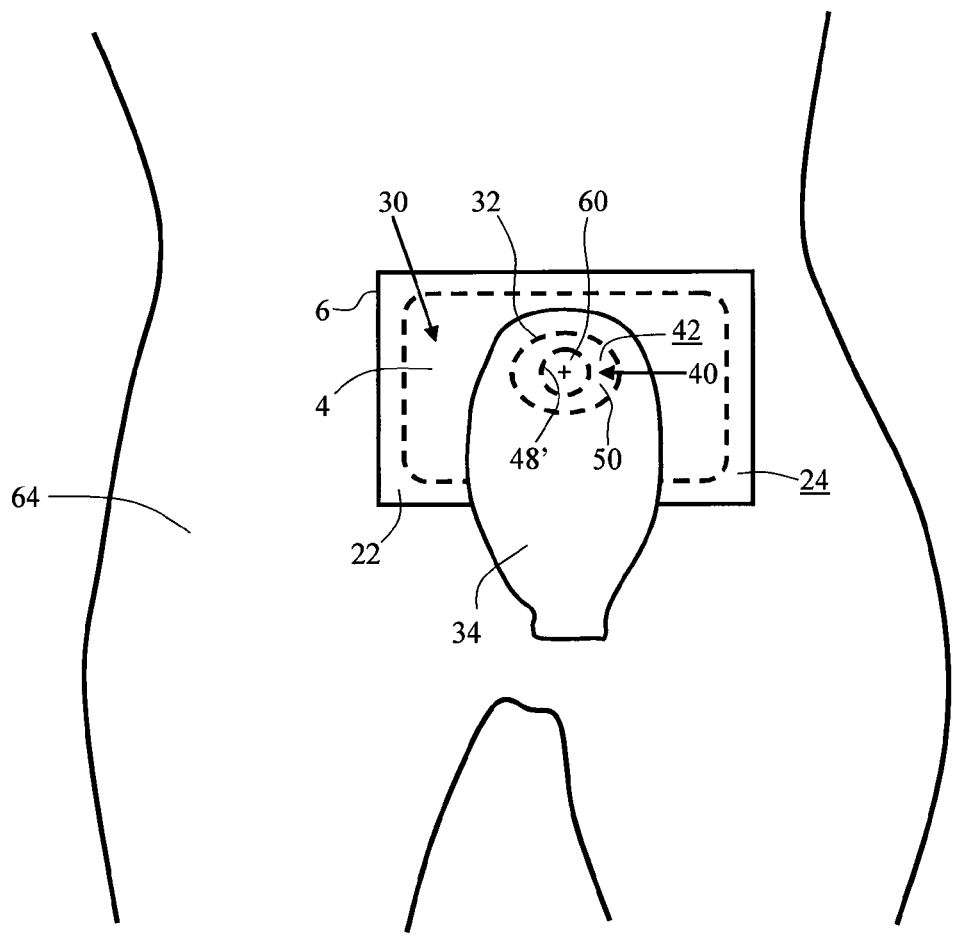

FIG. 8 shows, in section, an attachment plate and a stoma waste pouch mounted onto a body together with a stoma-leakage collecting device, wherein the figure also shows an extracted intestine extending outward from a stoma on the body and into the stoma waste pouch via an opening in the attachment plate; and FIG. 9 shows, in principle and in smaller scale, the same as that shown in FIG. 8, but wherein FIG. 9 shows, in perspective, an attachment plate and a stoma waste pouch mounted onto a body together with a stoma-leakage collecting device.

The figures are schematic and merely show details and equipment being essential to the understanding of the invention. Further, the figures may be somewhat distorted with respect to relative dimensions of details and components shown in the figures, and/or the figures may be somewhat simplified with respect to the shape and richness of detail of such details and components. Hereinafter, equal, equivalent or corresponding details in the figures will be designated substantially the same reference numerals.

SPECIFIC DESCRIPTION OF THE EXEMPLARY EMBODIMENTS

Figure 1:
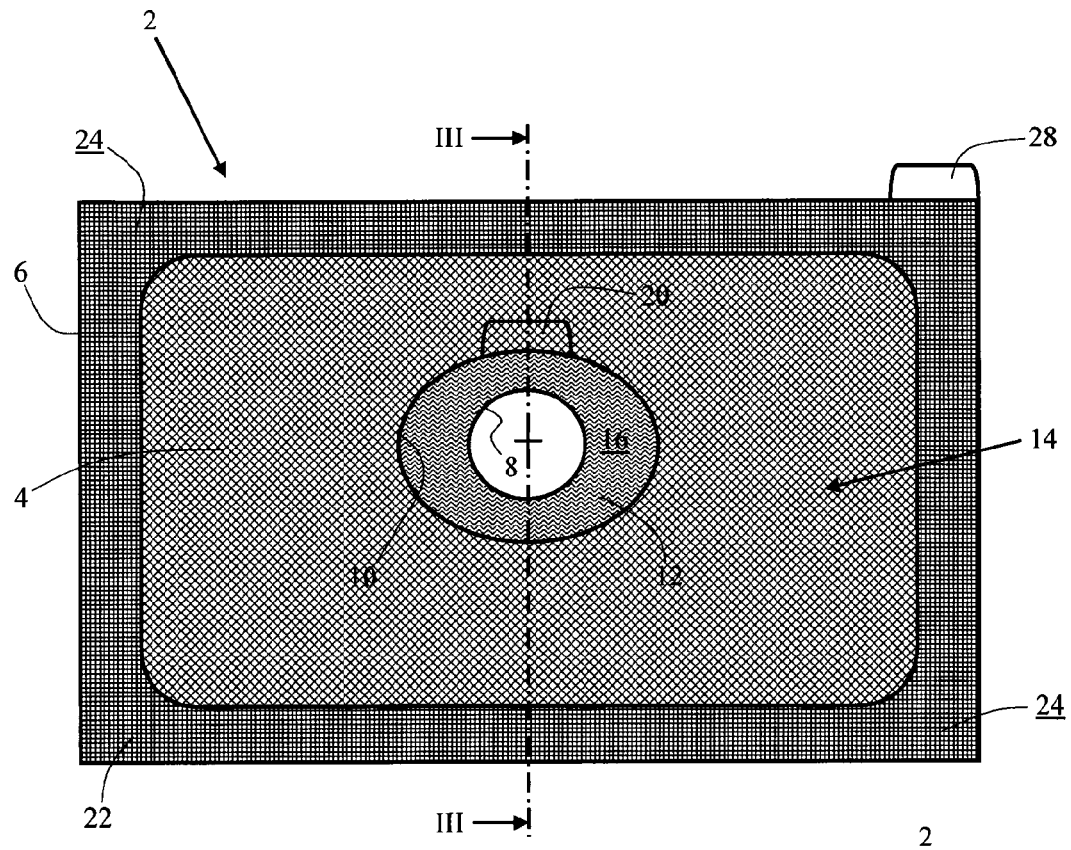
FIG. 1 shows, in plan view, an embodiment of a stoma-leakage collecting device according to the invention, wherein the figure shows an inside of the collecting device, and wherein the figure also shows a section line III-III.
Figure 2:
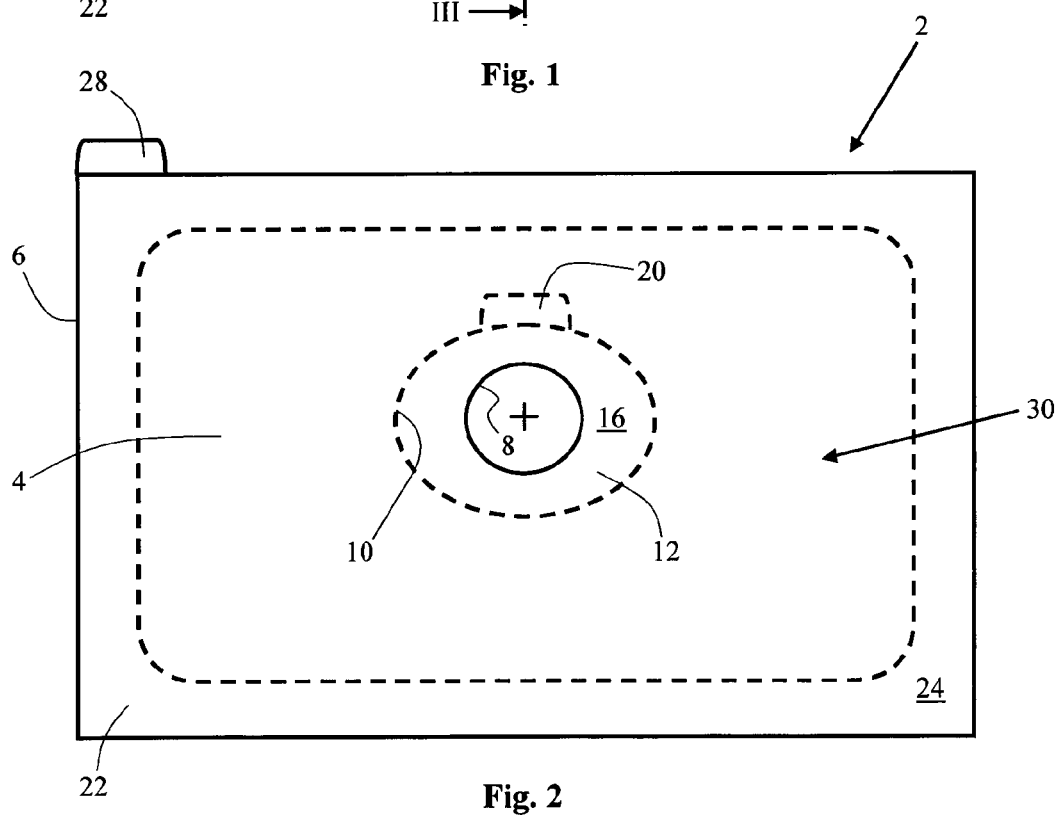
FIG. 2 shows, in plan view, an outside of the stoma-leakage collecting device according to FIG. 1.
Figure 3:
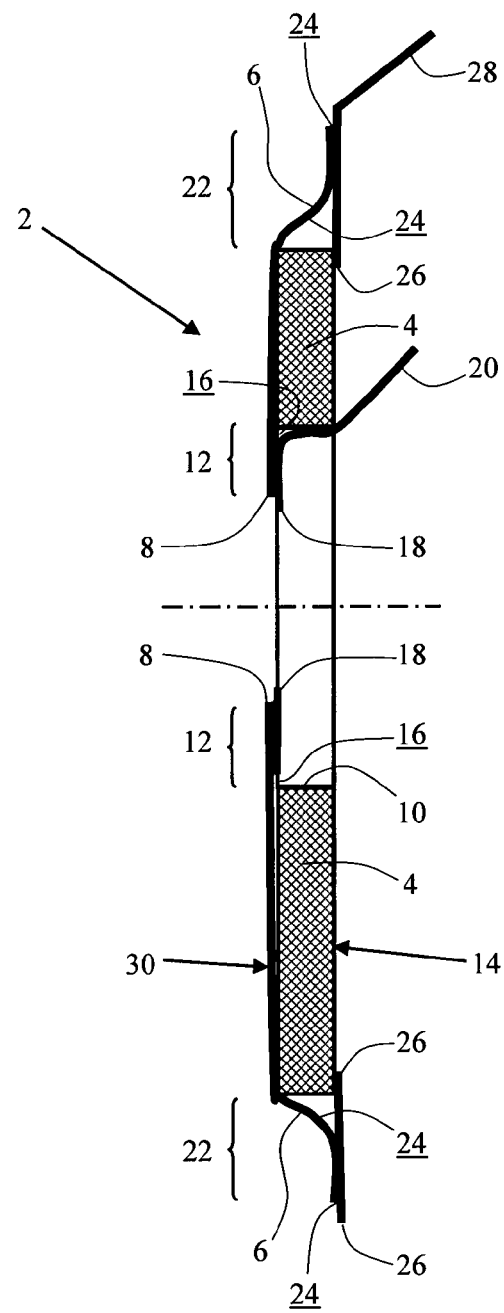
FIG. 3 shows, in larger scale, a cross-section of the stoma-leakage collecting device, as viewed along section line III-III in FIG. 1.

FIGS. 1-3 show an embodiment of a stoma-leakage collecting device 2 according to the invention. As shown best in FIG. 1, the collecting device 2 comprises, among other things, an inner, liquid-absorbent material 4, which for example comprises a so-called super-absorbent fabric known from nappy products, and an outer, liquid-tight material 6, for example a plastics material, covering the inner material 4. In this embodiment, the inner material 4 and the outer material 6 are connected to each other, for example with glue, but the materials 4 and 6 may also be releasably arranged relative to each other. Further, the collecting device 2 comprises an opening 8 through the outer material 6 and also a somewhat larger opening 10 through the inner material 4. A radially inner rim area 12 located on an inside 14 of the collecting device 2 and around the opening 8 in the outer material 6, and also within the opening 10 in the inner material 4, is provided with a first adhesive agent 16. In order to avoid that the adhesive agent 16 attaches to unwanted places, the inner rim area 12 and the adhesive agent 16 are covered by a releasable cover paper 18 (cf. FIG. 3) provided with a first gripping tab 20. Yet further, a radially outer rim area 22 of the collecting device 2 is provided with a second adhesive agent 24 on the inside 14 of the collecting device 2. In order to avoid that the adhesive agent 24 attaches to unwanted places, the outer rim area 22 and the adhesive agent 24 are covered by a releasable cover strip 26 (cf. FIG. 3) provided with a second gripping tab 28. FIG. 2 shows the collecting device 2 according to FIG. 1, as viewed from the outside 30 of the collecting device 2. FIG. 3, however, shows a cross-section through the collecting device 2, as viewed along section line III-III in FIG. 1.

Figure 4:
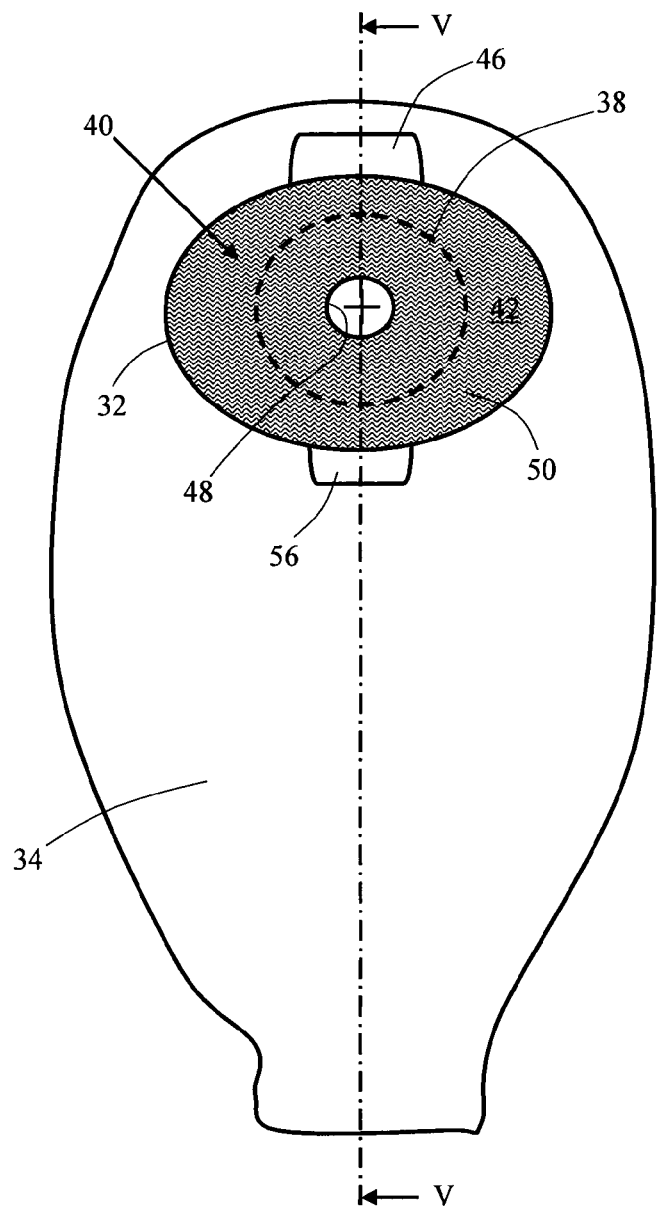
FIG. 4 shows an embodiment of an attachment plate according to the invention, wherein the attachment plate is provided with a stoma waste pouch mounted around an opening on an outside of the attachment plate, wherein the figure also shows a section line V-V.
Figure 5:
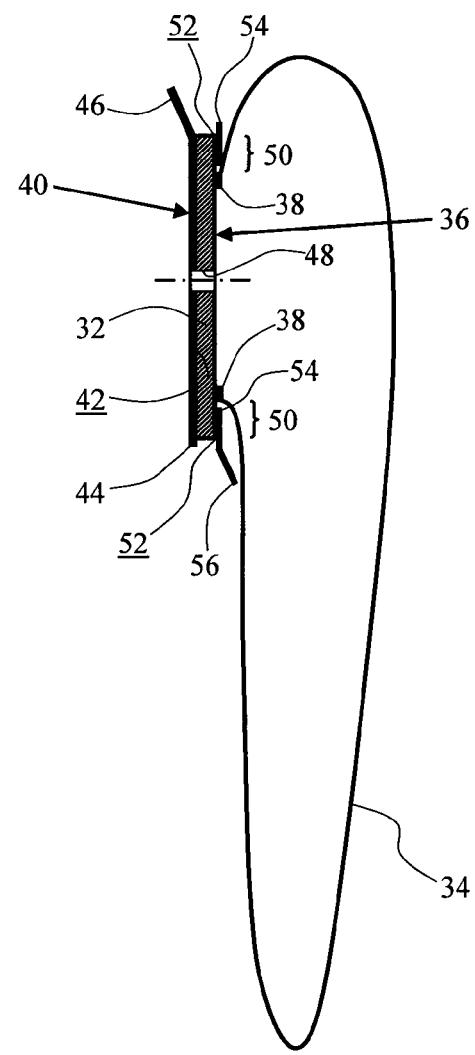
FIG. 5 shows a cross-section of the attachment plate and the stoma waste pouch according to FIG. 4, as viewed along section line V-V in FIG. 4.

FIGS. 4 and 5 show an embodiment of an attachment plate 32 according to the invention, wherein the attachment plate 32 in this embodiment is oval. The figures also show a stoma waste pouch 34 attached in a liquid-tight manner to an outside 36 of the attachment plate 32 via a continuous glue rim 38. In other embodiments (not shown in the figures), such an attachment plate may be releasably attached to a stoma waste pouch. The outside 36 of the attachment plate 32 is shown, among other places, in FIG. 5, which shows a cross-section through the attachment plate 32 and the stoma waste pouch 34, as viewed along section line V-V in FIG. 4. Further, FIG. 4 shows an inside 40 of the attachment plate 32 provided with a third adhesive agent 42. In order to avoid that the adhesive agent 42 attaches to unwanted places, the inside 40 of the attachment plate 32 and the adhesive agent 42 are covered by a releasable cover paper 44 (cf. FIG. 5) provided with a third gripping tab 46. The attachment plate 32 is formed from a relatively thin and flexible plastics material provided with a central stoma communication opening 48, which possibly may be extended outward to the glue rim 38 when required, for example through clipping or cutting of the plastics material around the opening 48. Yet further, the area between the periphery of the attachment plate 32 and the central opening 48 forms a radially outer rim area 50. In this embodiment, the outside 36 of the radially outer rim area 50 of the attachment plate 32 is provided with a fourth adhesive agent 52 for liquid-tight attachment to an inside 14 of the present stoma-leakage collecting device 2. In order to avoid that the adhesive agent 52 attaches to unwanted places, the rim area 50 of the attachment plate 32 and the adhesive agent 52 is covered by a releasable cover strip 54 (cf. FIG. 5) provided with a fourth gripping tab 56.

Figure 6:
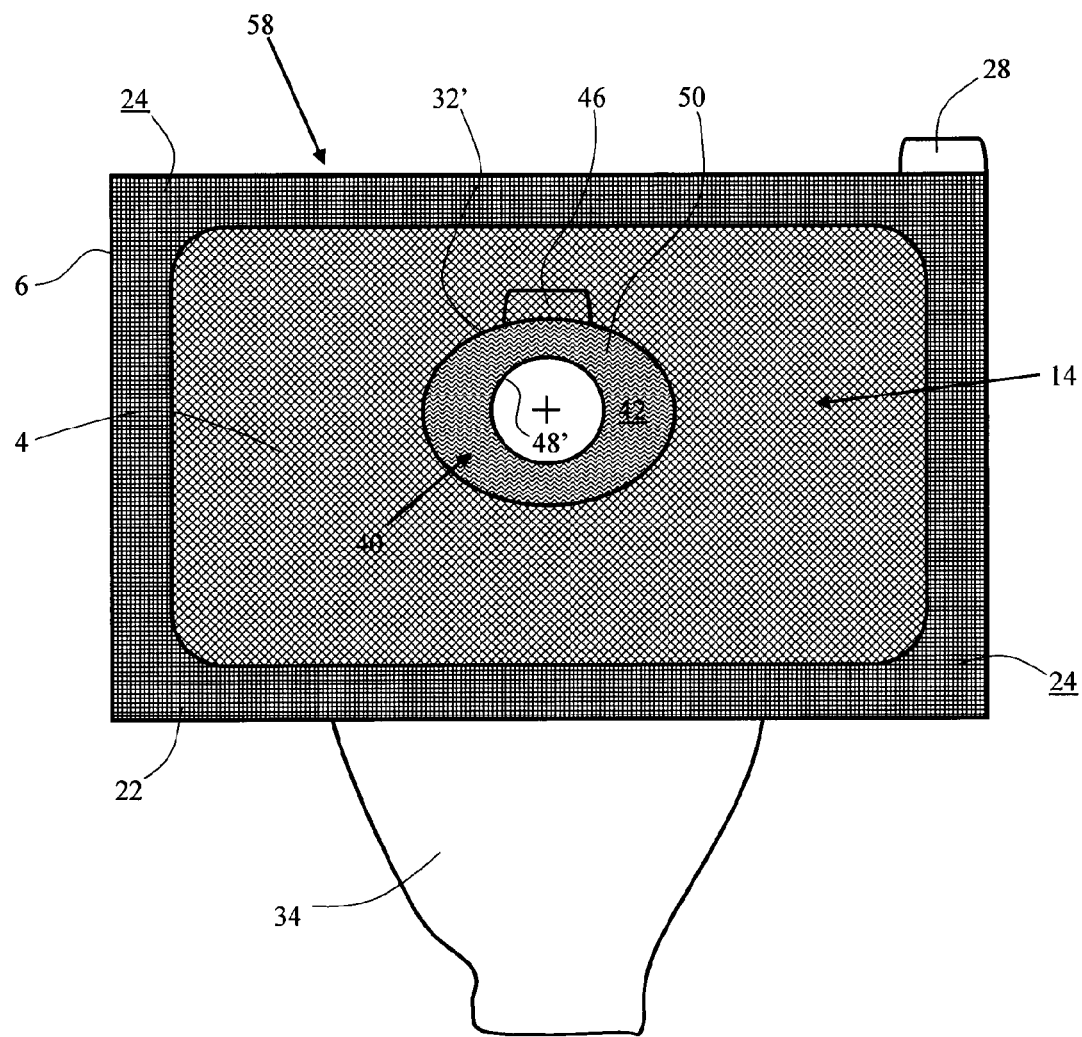
FIG. 6 shows, in plan view, an embodiment of an assembly according to the invention, wherein the figure shows an inside of the assembly, and wherein the figure shows a stoma-leakage collecting device according to FIGS. 1-3 connected together with an ordinary, per se attachment plate with a stoma waste pouch mounted thereon.
Figure 7:
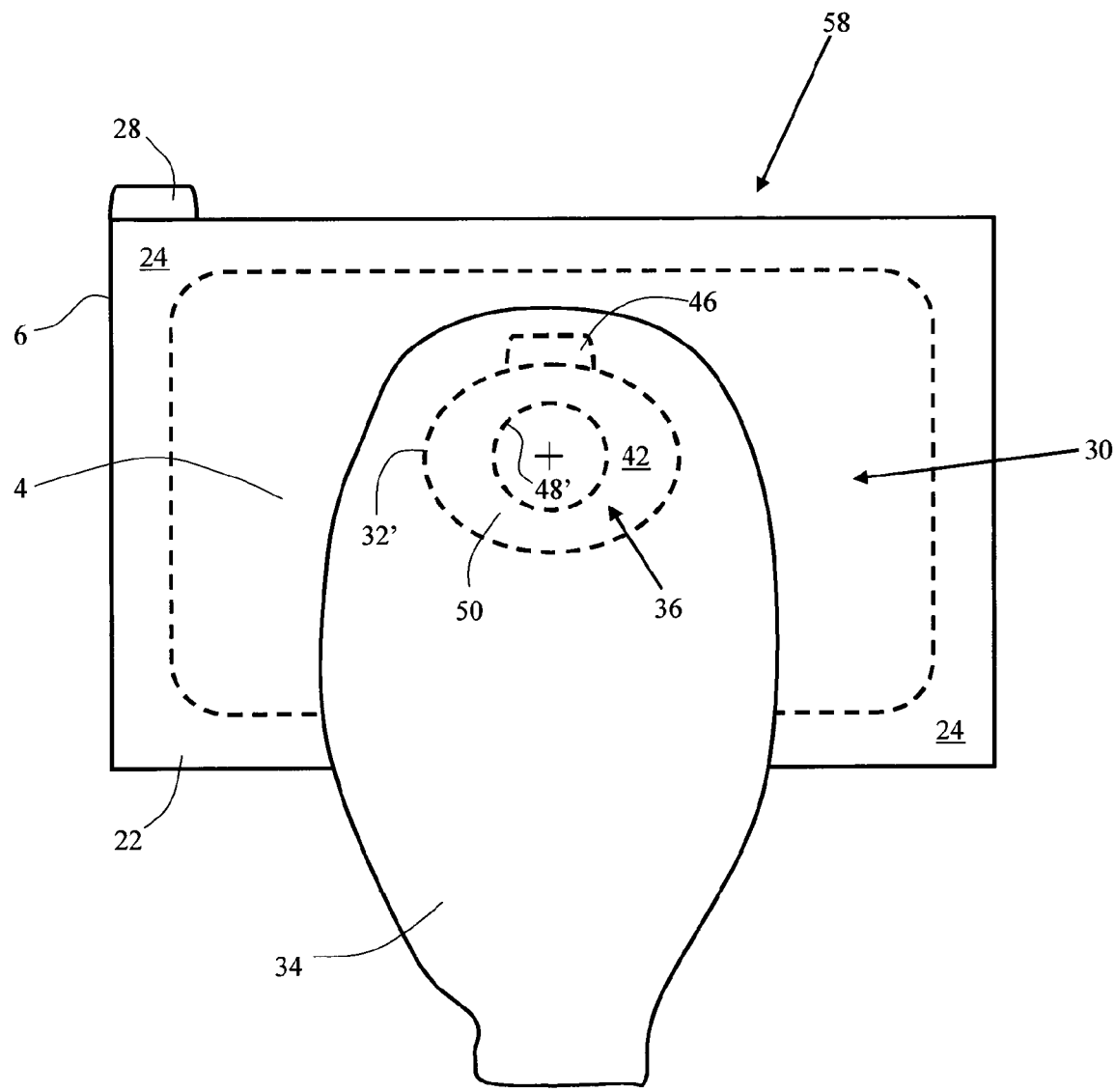
FIG. 7 shows, in plan view, an outside of the assembly according to FIG. 6.

FIGS. 6 and 7 show an embodiment of an assembly 58 according to the invention, wherein the figures show a stoma-leakage collecting device 2 according to FIGS. 1-3 assembled with an ordinary, per se attachment plate 32' of an oval shape having a stoma waste pouch 34 mounted thereon. This ordinary attachment plate 32' is approximately identical to the attachment plate 32 according to FIGS. 4 and 5, but the outside 36 of the attachment plate 32' lacks said fourth adhesive agent 52 and cover strip 54 from the attachment plate 32. The assembly 58 therefore comprises said inner, liquid-absorbent material 4 and said outer, liquid-tight material 6 covering the inner material 4. At the inside 14 thereof, the radially outer rim area 22 of the collecting device 2 is provided with said second adhesive agent 24 and also a releasable cover strip 26 (not shown in FIGS. 6 and 7) with a second gripping tab 28, wherein the cover strip 26 covers the outer rim area 22. Further, the attachment plate 32' is disposed within the opening 10 through the inner material 4 of the collecting device 2, and such that the opening 10 fits in a tight-fitting manner around the oval periphery of the attachment plate 32'. At the inside 40 thereof, the attachment plate 32' is also provided with said third adhesive agent 42 and also a releasable cover paper 44 (not shown in FIGS. 6 and 7) with a third gripping tab 46, wherein the cover paper 44 covers the inside 40. An enlarged stoma communication opening 48' is also formed through the attachment plate 32' for insertion of an extracted intestine 60 via a stoma 62 on a body 64 (cf. FIG. 8). Yet further, said first adhesive agent 16 on the inside 14 of the radially inner rim area 12 of the collecting device 2, the rim area 12 of which is located around the opening 8 in the outer, liquid-tight material 6 of the collecting device 2, has already been fixedly adhered to the radially outer rim area 50 of the attachment plate 32', the area of which is at the outside 36 of the attachment plate 32'. In this manner, the radially inner rim area 12 of the collecting device 2 is connected in a liquid-tight manner to the radially outer rim area 50 of the attachment plate 32'. In other embodiments (not shown in the figures), such a liquid-tight connection may be carried out in other ways, for example by virtue of the inner rim area 12 of the collecting device 2 being integrated together with the outer rim area 50 of the attachment plate 32'. For example, such integration may be carried out via fusion welding of the rim areas 12, 50, or by integrating the rim areas 12, 50 together via a mould casting process.

For the sake of good order, reference is also made to FIG. 6 showing the inside 14, 40 of the assembly 58, whereas FIG. 7 shows the outside 30, 36 of the assembly 58.

Reference is now made to FIG. 8, which shows a section through an attachment plate 32 (or attachment plate 32') and a stoma waste pouch 34 mounted onto said body 64 together with a stoma-leakage collecting device 2 according to the invention. The figure also shows said extracted intestine 60 extending outward through a stoma 62 on the body 64 and into the stoma waste pouch 34 via an enlarged stoma communication opening 48 (or opening 48') in the attachment plate 32, 32'. FIG. 9 shows, in principle, the same elements as those shown in FIG. 8, but FIG. 9 shows the elements viewed from a front side of the body 64. With reference to the preceding embodiments, this configuration of elements may be disposed on a body 64 in different ways, which will be explained in further detail hereinafter.

The simplest way of achieving such a configuration is to place an assembly 58, as shown in FIGS. 6 and 7, directly onto the body 64. Before placing the assembly 58 onto the body 64, the cover paper 44 is removed from the attachment plate 32' by grabbing hold of the gripping tab 46 and pulling the cover paper 44 away from the adhesive agent 42 on the inside 40 of the attachment plate 32'. Additionally, the cover strip 26 is removed from the collecting device 2 by grabbing hold of the gripping tab 28 and pulling the cover strip 26 away from the adhesive agent 24 on the inside 14 of the radially outer rim area 22 of the collecting device 2. Then the enlarged stoma communication opening 48' in the attachment plate 32' is placed around the extracted intestine 60 and the stoma 62. Finally, the adhesive agent 42 on the attachment plate 32', and also the adhesive agent 24 on the outer rim area 22 of the collecting device 2, is adhered to the body 64, thereby forming a liquid-tight connection to the body 64.

An alternative way of achieving such a configuration is to use a stoma collecting device according to the invention, for example a collecting device 2 as shown in FIGS. 1-3. First, an ordinary attachment plate 32', which has a stoma waste pouch 34 mounted thereon, is adhered directly onto the body 64 and around the extracted intestine 60 and the stoma 62. Then, the waste pouch 34 is folded in toward the centre thereof, whereupon the folded-up pouch 34 is inserted through the openings 8 and 10 in a stoma-leakage collecting device 2 according to FIGS. 1-3. By so doing, the radially inner rim area 12 of the collecting device 2 will be located between the attachment plate 32' and the stoma waste pouch 34. The cover paper 18 is then removed from the inner rim area 12 by grabbing hold of the gripping tab 20 and pulling the cover paper 18 away from the adhesive agent 16 on the inside 14 of the liquid-tight material 6 of the collecting device 2. Thereafter, the adhesive agent 16 on the inner rim area 12 is adhered to an outer rim area of the ordinary attachment plate 32', thereby forming a liquid-tight connection to the radially outer rim area 50 of the attachment plate 32'. Additionally, the cover strip 26 is removed from the collecting device 2 by grabbing hold of the gripping tab 28 and pulling the cover strip 26 away from the adhesive agent 24 on the inside 14 of the radially outer rim area 22 of the collecting device 2. Finally, the adhesive agent 24 on this outer rim area 22 is adhered to the body 64, thereby forming a liquid-tight connection to the body 64.

A further alternative way of achieving said configuration of elements on a body 64 is to use an attachment plate 32 according to the invention, for example the attachment plate shown in FIGS. 4 and 5. The method is mainly as described in the preceding example, however with the exception that it is the cover strip 54 on the outside 36 of the radially outer rim area 50 of the attachment plate 32 that is removed instead of the cover paper 18 on the inner rim area 12 of the collecting device 2 according to FIGS. 1-3. The cover strip 54 is removed by grabbing hold of the gripping tab 56 and pulling the cover strip 54 away from the adhesive agent 52 on the outside 36 of the outer rim area 50 of the attachment plate 32.

Then, the adhesive agent 52 on the outer rim area 50 is adhered to the inside 14 of the radially inner rim area 12 of the liquid-tight material 6 of the collecting device 2. By so doing, a liquid-tight connection between the outer rim area 50 of the attachment plate 32 and the inner rim area 12 of the collecting device 2 is formed. Additionally, the adhesive agent 24 on the outer rim area 22 of the collecting device 2 is adhered to the body 64, thereby forming a liquid-tight connection to the body 64, such as described in the preceding example.

The invention claimed is:

1. A stoma-leakage collecting device structured for use together with an attachment plate connected to a stoma waste pouch, the attachment plate being structured in a manner allowing it to be releasably attached to a body and around a stoma on the body;
    wherein the collecting device is comprised of a plate-shaped body having a surface which is larger than the surface of the attachment plate, and wherein the collecting device comprises:
        an inner, liquid-absorbent material for collection of leakage material from said stoma;
        an outer, liquid-tight material covering the inner material for inclusion of said leakage material; and
        an opening through the outer material and the inner material, respectively, wherein at least the opening in the outer material is structured in a manner allowing it to be placed around a corresponding stoma communication opening in the attachment plate, and wherein at least the opening in the outer material lies between an outer periphery of the stoma communication opening and an outer periphery of the attachment plate, wherein at least a radially inner rim area located around the opening in the outer material, is structured in a manner allowing it to be attached in a liquid-tight manner to a rim area of the attachment plate, whereby leakage between the collecting device and the attachment plate is prevented and wherein the outer material of the collecting device is directly attached in a liquid tight manner to the attachment plate on a side thereof facing away from the body.

2. The stoma-leakage collecting device according to claim 1, wherein at least the radially inner rim area of the collecting device is provided with an adhesive agent for liquid-tight attachment to the attachment plate.

3. The stoma-leakage collecting device according to claim 2, wherein the opening in the inner material is smaller than the attachment plate; and
    wherein also a radially inner rim area located around the opening in the inner material, is provided with an adhesive agent for liquid-tight attachment to the attachment plate.

4. The stoma-leakage collecting device according to claim 1, wherein the opening in the inner material is larger than the attachment plate, thereby allowing the attachment plate to be included therein.

5. The stoma-leakage collecting device according to claim 1, wherein the inner material is releasably arranged relative to the outer material, whereby the inner material is replaceable.

6. The stoma-leakage collecting device according to claim 1, wherein that a radially outer rim area of the collecting device is provided, with an adhesive agent for releasable and liquid-tight attachment to the body in an area located outside the attachment plate, whereby the collecting device is structured for complete liquid-tight inclusion of leakage material from said stoma.

7. The stoma-leakage collecting device according to claim 1, wherein a radially outer rim area of the collecting device is provided, with a continuous leakage barrier.

8. The stoma-leakage collecting device according to claim 1, wherein a radially outer rim area of the collecting device is structured so as to be elastically flexible for forcing the radially outer rim area against the body.

9. The stoma-leakage collecting device according to claim 1, wherein the collecting device is structured in a manner allowing it to be attached to the body in one of the following ways:
the collecting device is connected to a belt for attachment around the body;
the collecting device is incorporated in an elastic pad for attachment around the body; and
the collecting device is incorporated in a nappy for attachment around the body.

10. An attachment plate connected to a stoma waste pouch, the attachment plate being structured in a manner allowing it to be releasably attached to a body and around a stoma on the body;
wherein the attachment plate is structured for use together with a stoma-leakage collecting device comprised of a plate-shaped body, wherein the attachment plate has a surface which is smaller than the surface of the collecting device; and
wherein the collecting, device comprises:
an inner, liquid-absorbent material for collection of leakage material from said stoma;
an outer, liquid-tight material covering the inner material for inclusion of said leakage in and
an opening through the outer material and the inner material, respectively, wherein at least the opening in the outer material is structured in a manner allowing it to be placed around a corresponding, stoma communication opening in the attachment plate, and wherein at least the opening in the outer material lies between an outer periphery of the stoma communication opening and an outer periphery of the attachment plate, wherein a rim area of the attachment plate is structured in a manner allowing it to be attached in a liquid-tight manner to a radially inner rim area of the collecting device, said radially inner rim area being located at least around the opening in the outer material of the collecting device, whereby leakage between the attachment plate and the collecting device is prevented and wherein the outer material of the collecting device is directly attached in a liquid tight manner to the attachment plate on a side thereof facing away from the body.

11. The attachment plate according to claim 10, wherein the rim area of the attachment plate is provided with an adhesive agent for liquid-tight attachment to the radially inner rim area of the collecting device.

12. An assembly of a stoma-leakage collecting device and an attachment plate connected to a stoma waste pouch, the attachment plate being structured in a manner allowing it to be releasably attached to a body and around a stoma on the body;
wherein the collecting device is comprised of a plate-shaped body having a surface which is larger than the surface of the attachment plate, and wherein the collecting device comprises:
an inner, liquid-absorbent material for collection of leakage material from said stoma;
an outer, liquid-tight material covering the inner material for inclusion of said leakage material; and
an opening through the outer material and the inner material, respectively, wherein at least the opening in the outer material is placed around a corresponding stoma communication opening in the attachment plate, and wherein at least the opening in the outer material lies between an outer periphery of the stoma communication opening and an outer periphery of the attachment plate, wherein a radially inner rim area of the collecting device located at least around the opening in the outer material, of the collecting device, is connected in a liquid-tight manner to a rim area of the attachment plate, whereby leakage between the collecting device and the attachment plate is prevented and wherein the outer material of the collecting device is directly attached in a liquid tight manner to the attachment plate on a side thereof facing away from the body.

13. The assembly according to claim 12, wherein the radially inner rim area of the collecting device and the rim area of the attachment plate are connected in a liquid-tight manner in one of the following ways:
the radially inner rim area of the collecting device is fixedly adhered to the rim area of the attachment plate; and
the radially inner rim area of the collecting device and the rim area of the attachment plate are integrated together.

14. The assembly according to claim 12, wherein the inner material of the collecting, device is releasably arranged relative to the outer material of the collecting device, whereby the inner material is replaceable.

15. The assembly according to claim 12, wherein a radially outer rim area of the collecting device is provided with an adhesive agent for releasable and liquid-tight attachment to the body in an area located outside the attachment plate, whereby the assembly is structured for complete liquid-tight inclusion of leakage material from said stoma.

16. The assembly according to claim 12, wherein a radially outer rim area of the collecting device is provided with a continuous leakage barrier.

17. The assembly according to claim 12, wherein a radially outer rim area of the collecting device is structured so as to be elastically flexible for forcing the radially outer rim area against the body.

18. The assembly according to claim 12, wherein the assembly is structured in a manner allowing it to be attached to the body in one of the following ways:
the assembly is connected to a belt for attachment around the body;
the assembly is incorporated in an elastic pad for attachment around the body; and
the assembly is incorporated in a nappy for attachment around the body.

19. A stoma-leakage collecting device structured for use together with an attachment plate for a stoma waste pouch, the attachment plate being structured in a manner allowing it to be releasably attached to a body and around a stoma on the body;
wherein the collecting device is comprised of a plate-shaped body having a surface which is larger than the surface of the attachment plate, and wherein the collecting device comprises:
an inner, liquid-absorbent material for collection of leakage material from said stoma;
an outer, liquid-tight material covering the inner material for inclusion of said leakage material; and
an opening through the outer material and the inner material, respectively, wherein at least the opening in the outer material is structured in a manner allowing it to be placed around a corresponding stoma communication opening in the attachment plate, and wherein at least the opening, in the outer material lies between an outer periphery of the stoma communication opening and an outer periphery of the attachment plate, wherein at least a radially inner rim area located around the opening in the outer material, is structured in a manner allowing it to be attached in a liquid-tight manner to a rim area of the attachment plate, whereby leakage between the collecting device and the attachment plate is prevented, wherein the opening in the inner material is larger than the attachment plate, thereby allowing the attachment plate to be included therein.

20. A stoma-leakage collecting device structured thr use together with an attachment plate for a stoma waste pouch, the attachment plate being structured in a manner allowing it to be releasably attached to a body and around a stoma on the body;

wherein the collecting device is comprised, of a plate-shaped body having a surface which is larger than the surface of the attachment plate, and wherein the collecting device comprises:

an inner, liquid-absorbent material for collection of leakage material from said stoma;

an outer, liquid-tight material covering the inner material for inclusion of said leakage material; and an opening through the outer material and the inner material, respectively, wherein at least the opening in the outer material is structured in a manner allowing it to be placed around a corresponding stoma communication opening in the attachment plate, and wherein at least the opening in the outer material lies between an outer periphery of the stoma communication opening and an outer periphery of the attachment plate, wherein at least a radially inner rim area located around the opening in the outer material, is structured in a manner allowing it to be attached in a liquid-tight manner to a rim area of the attachment plate, whereby leakage between the collecting device and the attachment plate is prevented, wherein the inner material is releasably arranged relative to the outer material, whereby the inner material is replaceable.

21. An assembly of a stoma-leakage collecting device and an attachment plate for a stoma waste pouch, the attachment plate being structured in a manner allowing it to be releasably attached to a body and around a stoma on the body;

wherein the collecting device is comprised of a plate-shaped body having a surface which is larger than the surface of the attachment plate, and wherein the collecting device comprises:

an inner, liquid-absorbent material for collection of leakage material from said stoma;

an outer, liquid-tight material covering the inner material for inclusion of said leakage material; and an opening through the outer material and the inner material, respectively, wherein at least the opening in the outer material is placed around a corresponding stoma communication opening in the attachment plate, and wherein at least the opening in the outer material lies between an outer periphery of the stoma communication opening and an outer periphery of the attachment plate, wherein as radially inner rim area of the collecting device located at least around the opening in the outer material of the collecting device, is connected in a liquid-tight manner to a rim area of the attachment plate, whereby leakage between the collecting device and the attachment plate is prevented, wherein the inner material of the collecting device is releasably arranged relative to the outer material of the collecting device, whereby the inner material is replaceable.

* * * * *